US005705128A

United States Patent [19]

Worthington et al.

[11] Patent Number: 5,705,128

[45] Date of Patent: Jan. 6, 1998

[54] SAMPLE EXCHANGE SYSTEM

[76] Inventors: James N. Worthington, 231-B Otto St., Port Townsend, Wash. 98368; Joseph R. Munn, 328 Munn Rd., Quilcene, Wash. 98376

[21] Appl. No.: 516,133

[22] Filed: Aug. 17, 1995

[51] Int. Cl.[6] .................... G01N 33/00

[52] U.S. Cl. .................... 422/63; 422/62; 422/64; 422/6; 422/58; 422/104; 436/714

[58] Field of Search .................... 422/62, 63, 66, 422/68.1, 99, 101, 102, 104, 58, 64, 65; 436/174

[56] References Cited

U.S. PATENT DOCUMENTS

| | | | |
|---|---|---|---|
| 4,959,976 | 10/1990 | Matsuda et al. | 62/271 |
| 5,009,850 | 4/1991 | Bell | 422/99 |
| 5,102,624 | 4/1992 | Muraishi | 422/64 |
| 5,120,506 | 6/1992 | Saito et al. | 422/66 |
| 5,169,600 | 12/1992 | Ishizaka et al. | 422/66 |

*Primary Examiner*—Harold Y. Pyon
*Attorney, Agent, or Firm*—Linval B. Castle

[57] ABSTRACT

An exchange system whereby a sample to be tested in a chamber, such as a vacuum chamber, may be entered and withdrawn with a minimum of loss of vacuum. The sample is mounted on a circular platen having six wedge shaped ramps in the periphery. A sample fork, in an anti-chamber that is connected to the chamber by a sealable door and can be maneuvered axially and rotationally about that axis, has three spring fingers that can be locked into the wedges to secure the platen. a sample dock, located in the main chamber, is axially aligned with the fork and has three fingers that engage the remaining three ramps when the platen enters the chamber. Rotation of the fork and the platen will cause the dock fingers to grasp the platen while the fork fingers release it, thereby transferring the platen into the chamber. Varied tests may then be performed under hot and cold vacuum conditions. Removal of the platen is done by reversing the procedure.

6 Claims, 4 Drawing Sheets

SAMPLE EXCHANGE SYSTEM

This invention relates generally to laboratory equipment and in particular to a mechanism for transferring a specimen between two environments.

BRIEF SUMMARY OF THE INVENTION

In testing of small components it is often necessary to pass the component from one environment into a different environment. For example, it may be necessary to transfer a sample into a radiation beam for testing or from room temperature into a test chamber containing a gas or corrosive or a chamber at a sub-freezing temperature or under a high vacuum.

The invention described herein is for a sample exchange system for transferring a sample to and from a test fixture in another environment, in this instance, a test or vacuum chamber where various tests are to be performed. The sample exchange system includes a transfer fork to be located outside a test chamber and which can grasp a sample platen which supports the sample or specimen to be tested in the chamber, and a sample dock located in the chamber for receiving the sample platen from the transfer fork.

The transfer fork is generally within a small anti-chamber that is coupled through a door to a small port in the main chamber wall. If the main chamber is a vacuum chamber, the anti-chamber should have an access door that is sealable so that a platen may be attached for insertion into the main chamber after the access door has been closed. The transfer fork is attached to a longitudinal shaft that is manipulated either manually or robotically from outside the anti-chamber to either rotate the transfer fork or move it linearly through the port of the main chamber.

The transfer fork has three spring fingers which grasp three of six wedge shaped ramps in the periphery of a sample platen to which is attached a specimen or sample to be tested in the main chamber. Such a sample may be a small electronic part to be tested under extreme heated and/or vacuum conditions.

The sample dock within the main chamber also has three spring fingers for grasping the remaining three ramps of the sample platen being passed to it by the transfer fork. The sample exchange is made as follows: the three fingers engage the the bottom of the ramps and a small rotational movement of the transfer fork engages the sample platen upon the sample dock while releasing the platen from the transfer fork. Reversing the direction of rotation will reverse the procedure and lock the platen back on the transfer fork.

The transfer dock within the main chamber may be a simple dock for merely holding the sample platen in the environment of the main chamber or it may be specialized to perform certain test functions. Thus, the transfer dock may be equipped with heating coils for rapid heating of the sample or may be rapidly chilled by liquid nitrogen. It may have contacts on it for contacting thermocouples or other samples that require monitoring for electrically testing in the environment. It may have the feature of drawing a sample into contact with the dock body for quick cooling or heating.

DESCRIPTION OF THE DRAWINGS

In the drawings which illustrate a preferred embodiment of the invention.

DESCRIPTION OF THE PREFERRED EMBODIMENT

Figure 1:
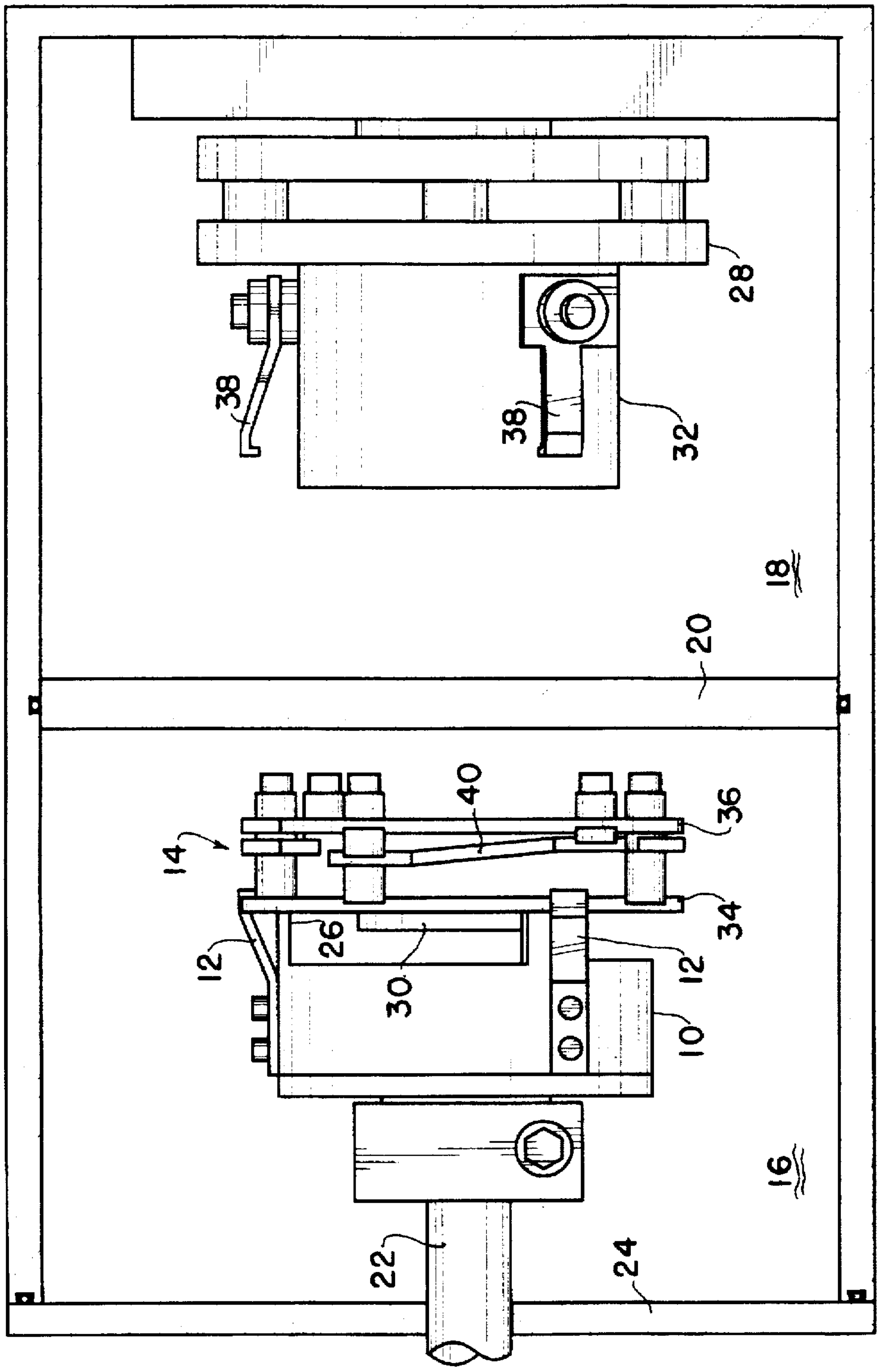
FIG. 1 illustrate a transfer fork with a sample platen and a typical transfer dock.

FIG. 1 illustrates a transfer fork 10 with three equally spaced spring fingers 12 around the periphery of its circular body grasping a sample platen 14. Fork 10 is located within a small anti-chamber 16 connected to a larger main chamber 18 and may be entered into the chamber 18 through a sealable door 20. The fork is attached to a shaft 22 and is both linearly and rotationally maneuverable by the shaft 22 from a point through a door 24 and outside of the anti-chamber.

Figure 2:
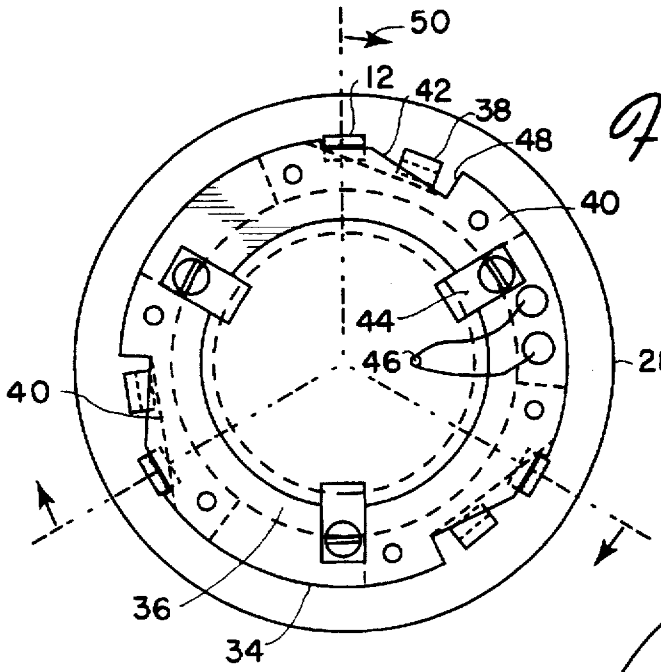
FIGS. 2, 3 and 4 illustrate the steps in transferring a platen from the transfer fork to the transfer dock.

The fork 10 is shown holding the platen 14 against extensions 26 from its circular body with the equally spaced leaf spring fingers 12 having 90° inward facing hooks at their ends which engage the periphery of the circular shaped platen 14. The platen has three equally spaced wedge shaped ramps in its surface extending from the platen periphery to a smaller diameter, as shown in FIG. 2, so that mounting the platen to the fork of FIG. 1 is easily accomplished by aligning the three fingers 12 within the small diameter portion of the ramps, pressing the platen against the extensions 26, and rotating the platen while holding the fork until the three fingers climb up the wedge shaped ramps to the periphery of the platen.

When the platen is properly mounted to the fork, as shown in FIG. 1, the door 24 is closed to seal the anti-chamber 16 and the door 20 is opened into the main chamber so that the fork 10 with the platen 14 may enter.

The sample platen 14 carries the sample to be locked to the sample dock 28 for testing in the main chamber 18. The platen may take many forms: it may be a single disc with three ramps for engaging the fork plus three more for coupling to a dock which only holds the platen in the main chamber; or the platen may be a more complex multi-disc type having a second disc with ramps that engages contacts on the dock for electrically testing a sample under extreme heat and/or cold conditions.

Figure 8:
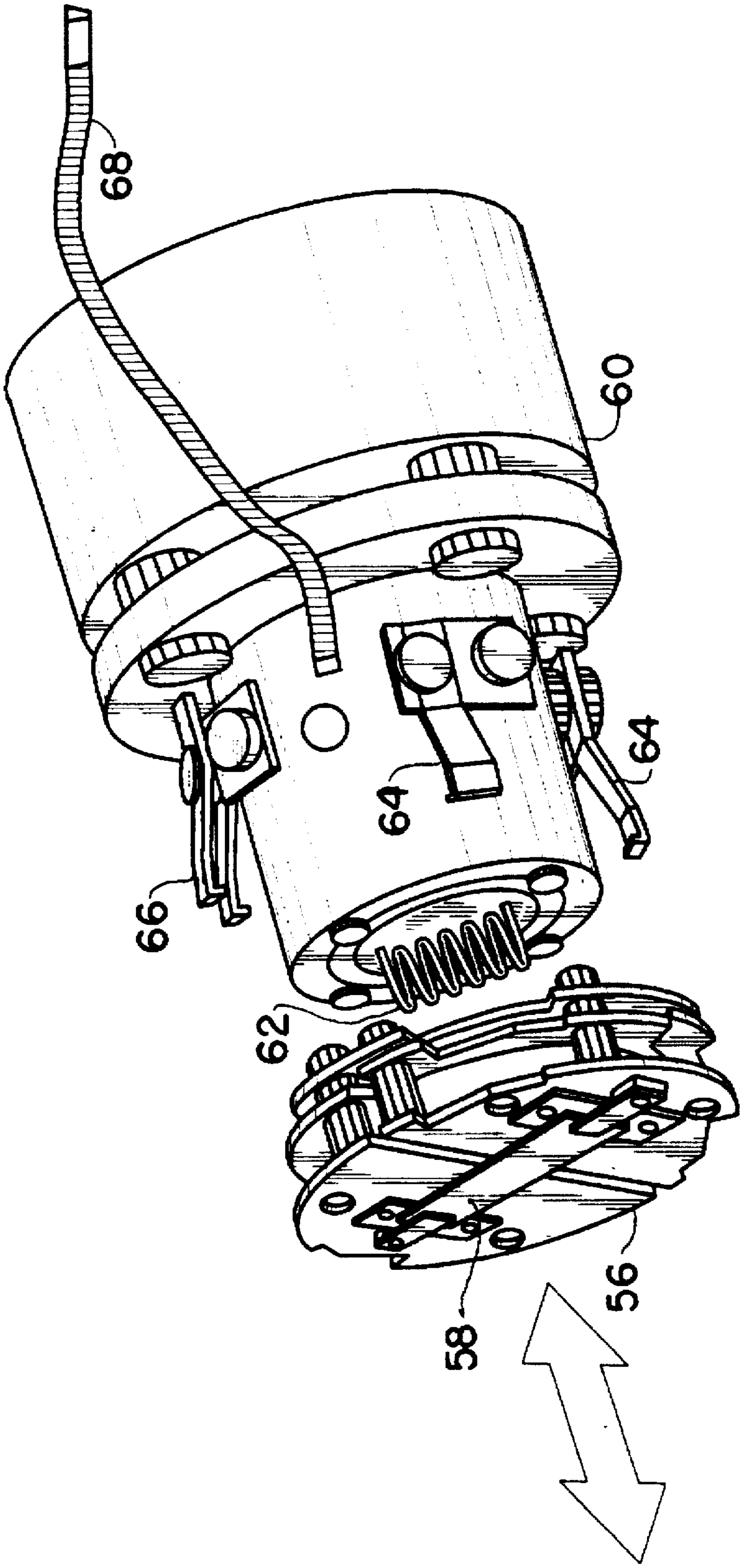
FIG. 8 illustrates a sample platen with a transfer dock that is equipped for rapid heating and cooling of a sample.

The sample platen 14 of FIG. 1 is of the more complex type for mounting to the sample dock 28 which is assumed to be electrically heated. The platen 14 holds, within an opening in the center of its disc, a sample 30 which must be held against the sample dock 28 which has a large extended tubular body 32. The illustrated platen therefore has two discs, 34, 36. Disc 34 holds the sample 30 and has three equally spaced ramps for engaging the fingers 12 of fork 10. Disc 34 is connected by standoff spacers to disc 36 which has three equally spaced ramps for engaging the fingers 38 of the dock 28 and which is annular with a central opening to permit entry of the tubular body 32 of the dock. In the platen illustrated for heat and cold testing of sample 30, it is to be assumed that it is important that the sample be held close to the body of the dock. Therefore the three ramps to be engaged by the fingers of the dock are also ramped away from the dock, as shown by ramp 40, so that the dock finger will draw the platen close as the platen is rotated into a locked position. Electrical information, such as thermocouple signals, bias or current flows, are transmitted between the platen and dock through the fingers which are shown to be insulated. If a sample is to be heated by passing electrical current through it the sample carrying disc of the platen is split with the sample stradding the two halves to act as a current path, as shown in FIG. 8. Thus, the platen may take any desired form as long as it has ramps for engagement with the transfer fork and the dock.

Figure 3:
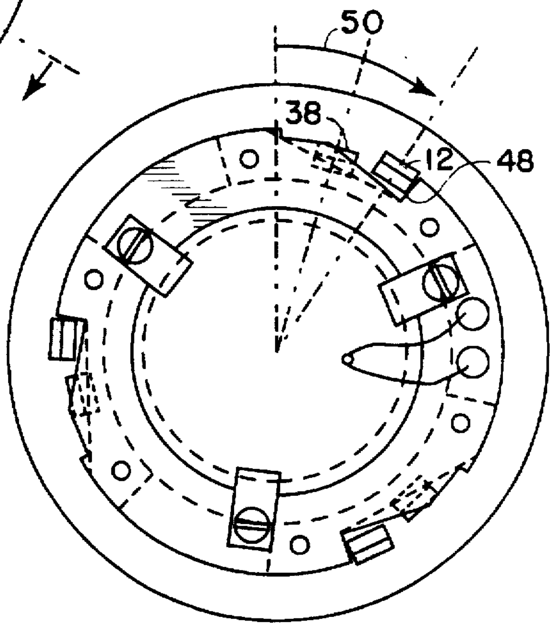
Figure 4:
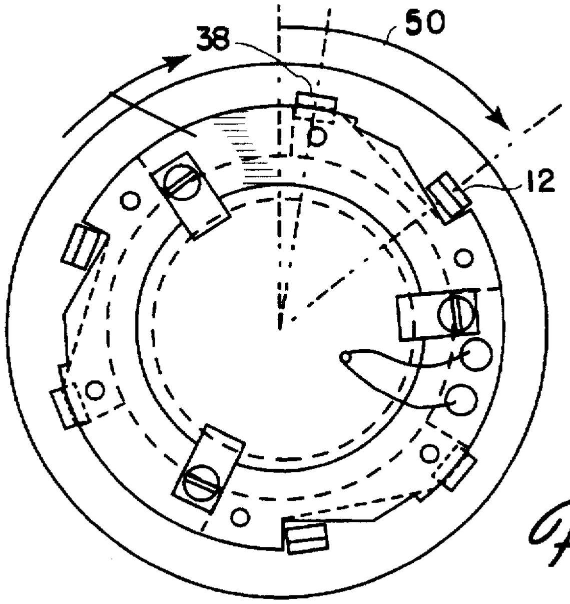

FIGS. 2, 3, and 4 illustrate steps in transferring the platen 14 of FIG. 1 from fork 10 to dock 28. The illustrations of FIGS. 2–4 are viewed from the fork, therefore the fingers 12 are shown in section grasping the ramps 42 of the disc 34. Disc 34 is shown with three clamps 44 for securing the sample and a thermocouple 46 connected to two insulated connectors on the disc. Also illustrated are three spring fingers 38 on the dock 28 positioned above the ramps 40. FIG. 2 represents the positions of the platen and the fork and dock fingers after mounting the platen on the fork and before the transfer begins by rotating the fork and platen in the direction of the arrow 50.

FIG. 3 shows the disengagement of the platen 34 from the fork fingers 12 by rotating the fork 10 until the fingers are freed of the ramp 42 and are abutting the lower end 48 of the ramp. The dock fingers 38 have not yet engaged their respective ramps.

FIG. 4 shows that further rotation of the fork 10 in the direction of arrow 50 against the ramp lower end 48 will force the dock fingers 38 to lock onto the periphery of the ramp 40 and will draw in the platen against the body of the dock, as previously described. At this point the fork fingers 12 are fully releasable from the platen and the fork may be withdrawn from the platen and from the main chamber 18 so that the port door 20 in the chamber may be closed to preserve its environment.

Figure 5:
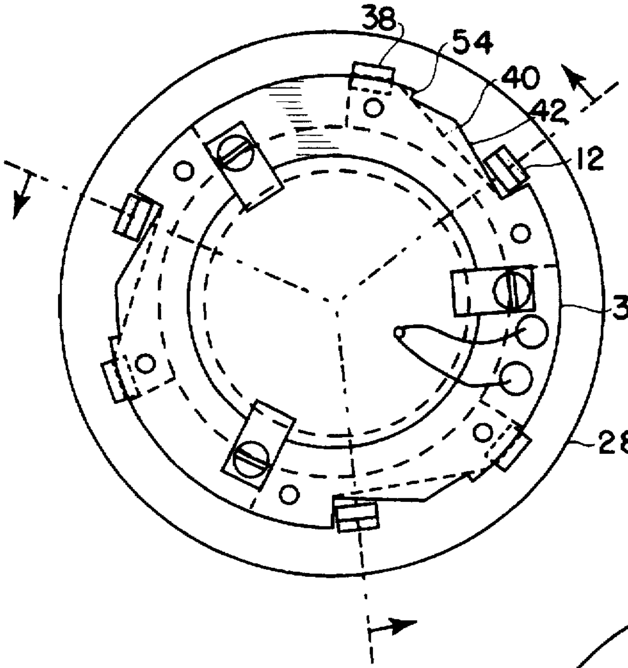
FIGS. 5, 6 and 7 illustrate the steps in transferring a platen from the transfer dock to the transfer fork.
Figure 6:
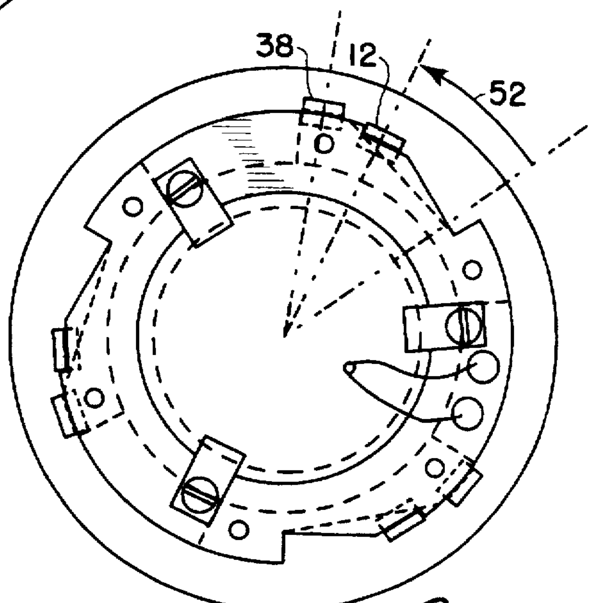
Figure 7:
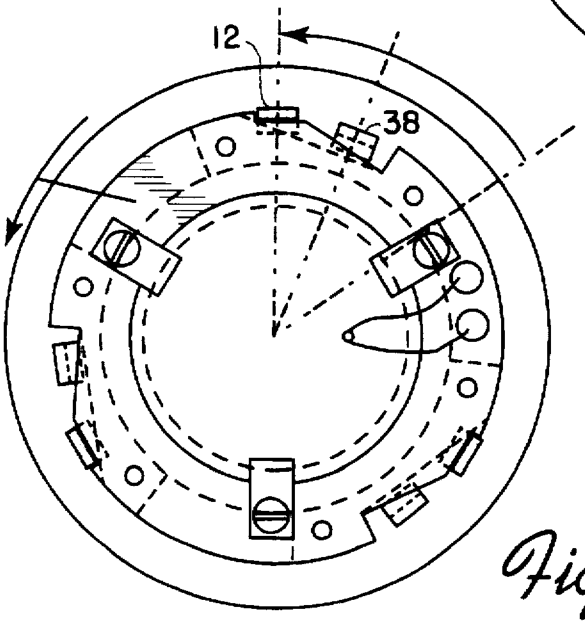

FIGS. 5, 6 and 7 show the reverse operation of transferring the platen from the dock back to the transfer fork. In FIG. 5, the positions of the dock fingers 38 and fork fingers 12 on their respective ramps are the same as shown in FIG. 4. Now, however, the port door 20 to the main chamber 18 has been opened and the fork 10 has been inserted to retrieve the platen. Note that the dock fingers 38 are grasping the periphery of the ramp 40 and the fork fingers 12 are in position over the ramp 42.

FIG. 6 shows that rotation of fork 10 in the direction of the arrow 52 will cause the fingers 12 to engage the ramp 42 and go to the upper ramp end abutment 54. The platen has not yet been rotated and the dock fingers 38 remain locked to its periphery.

FIG. 7 shows that further rotation of the fork 10 in the direction of the arrow 52 forces the fork finger 12 against the upper ramp end abutment 54, causing the platen to rotate and causing the dock fingers 38 to be freed from the ramp 40. The fork 10 with the platen 14 may then be withdrawn from the main chamber 18 and the port door 20 closed to preserve its environment.

FIG. 8 is a perspective view of a split platen 56 for testing a sample 58 that is to carry current through it. The sample 58 therefore straddles the split in the platen and the sample and its mounting clamps are suitably insulated. The sample dock 60 is shown with a heating coil 62 for radiantly heating the sample and with insulated fingers 64, one of which is provided with a spring backing piece 66 for giving greater contact force to its associated finger. A sample dock may have additional fingers for making electrical contact with the associated platen and sample. Thus, in FIG. 8, the dock 60 has three platen grasping fingers fingers, two of which are insulated copper and may be used for passing current through the sample. The third grasping finger and a fourth non-grasping finger may be for coupling to a thermocouple, and may even be made of thermocouple material, such as alumel and chromel and may be backed with a stainless steel spring. After heating, the dock of FIG. 8 may be cooled by introducing liquid nitrogen into the tubular body of the sample dock through the flexible tubing 58.

We claim:

1. A sample exchange system for transferring a sample between two environments, said exchange system comprising:

a circular platen having means for supporting the sample, said platen having at least six wedge shaped ramps in its periphery;

a transfer fork located in a first environment, said fork having a first and a second surface and a shaft on a central axis extending from its second surface, said fork being moveable along and rotatable about said axis, said fork having three equally spaced spring fingers extending from said first surface for entering a first three of said ramps in said platen and for grasping said platen upon a small rotation of said platen in a second direction;

a sample dock located in a second environment, said dock being axially aligned with said transfer fork for receiving said platen from said fork, said dock having three equally spaced fingers for entering the second three of said ramps in said platen and for grasping said platen upon rotation of said platen by said fork in a first direction whereby said platen is released from said transfer fork; wherein said circular platen includes a first circular disc having said first three of said ramps in its periphery for coupling to the fingers of said transfer fork, and a second disc coaxial with and spaced from said first disc and having said second of said ramps foor coupling to the said sample dock; and wherein said first circular disc is electrically insulated from said second disc and said first circular disc is divided into two semicircular sectors, said semicircular sectors being spaced from each other.

2. The sample exchange system claimed in claim 1 wherein said second environment is within an enclosed chamber, and wherein said transfer fork is separated from said chamber by a door.

3. The sample exchange system claimed in claim 1 wherein said circular platen includes a third partial disc having said second three of said ramps for coupling to the fingers of said dock, said third ramps being ramped back from said third disc toward said transfer fork whereby engagement with the fingers of said dock will draw said platen into tight engagement with said dock.

4. The sample exchange system claimed in claim 1 wherein said sample dock includes heating coils and refrigerant tubing for selectively heating and cooling a platen.

5. The sample exchange system claimed in claim 1 wherein said second disc ramps are insulated for electrical testing of said sample and wherein said second disc has additional connections for electrical testing.

6. The sample exchange system claimed in claim 5 wherein the fingers of said dock are electrical conductors, and wherein said dock contains spring contacts for contacting said additional connections on said platen.

* * * * *